US007025804B2

(12) United States Patent
Simmons et al.

(10) Patent No.: US 7,025,804 B2
(45) Date of Patent: Apr. 11, 2006

(54) METHOD FOR SEPARATING HYDROCARBON-CONTAINING GAS MIXTURES USING HYDROCARBON-RESISTANT MEMBRANES

(75) Inventors: John W. Simmons, Wilmington, DE (US); Sudhir Kulkarni, Wilmington, DE (US); Okan M. Ekiner, Wilmington, DE (US)

(73) Assignee: L'Air Liquide, Societe Anonyme A Directoire et Conseil De Surveillance Pour L'Etude et L'Exploitation Des Procedes Georges Claude, Paris (FR)

( * ) Notice: Subject to any disclaimer, the term of this patent is extended or adjusted under 35 U.S.C. 154(b) by 62 days.

(21) Appl. No.: 10/723,387

(22) Filed: Nov. 25, 2003

(65) Prior Publication Data

US 2004/0159233 A1    Aug. 19, 2004

Related U.S. Application Data

(63) Continuation-in-part of application No. 10/642,407, filed on Aug. 15, 2003, which is a continuation-in-part of application No. 10/353,210, filed on Jan. 27, 2003.

(60) Provisional application No. 60/508,940, filed on Oct. 6, 2003, provisional application No. 60/430,275, filed on Dec. 2, 2002, provisional application No. 60/430,327, filed on Dec. 2, 2002.

(51) Int. Cl.
*B01D 53/22* (2006.01)
*B01D 71/64* (2006.01)
*B01D 69/12* (2006.01)

(52) U.S. Cl. ............... 95/51; 95/45; 95/47; 95/50; 96/8; 96/10; 96/13; 96/14

(58) Field of Classification Search .......... 95/45, 95/47–55; 96/4, 8, 10, 12–14; 55/524, DIG. 5; 210/500.23, 500.39
See application file for complete search history.

(56) References Cited

U.S. PATENT DOCUMENTS

| | | | | |
|---|---|---|---|---|
| 4,080,744 A | * | 3/1978 | Manos | 34/340 |
| 4,113,628 A | | 9/1978 | Alegranti | |
| 4,120,098 A | * | 10/1978 | Manos | 34/337 |
| 4,230,463 A | * | 10/1980 | Henis et al. | 95/47 |
| 4,532,041 A | | 7/1985 | Shuey et al. | |
| 4,571,444 A | | 2/1986 | Black et al. | |
| 4,606,903 A | | 8/1986 | Hafez et al. | |
| 4,690,873 A | * | 9/1987 | Makino et al. | 96/10 |
| 4,705,540 A | | 11/1987 | Hayes | |
| 4,717,393 A | | 1/1988 | Hayes | |
| 4,717,394 A | * | 1/1988 | Hayes | 95/49 |
| 4,836,927 A | | 6/1989 | Wan | |
| 4,880,442 A | | 11/1989 | Hayes | |
| 4,897,092 A | * | 1/1990 | Burgoyne et al. | 95/54 |
| 4,932,982 A | * | 6/1990 | Hayes | 95/51 |
| 4,988,371 A | * | 1/1991 | Jeanes et al. | 95/53 |
| 5,015,270 A | * | 5/1991 | Ekiner et al. | 95/54 |
| 5,034,024 A | * | 7/1991 | Hayes | 95/54 |
| 5,042,992 A | * | 8/1991 | Blinka et al. | 95/51 |
| 5,055,116 A | * | 10/1991 | Kohn et al. | 95/47 |
| 5,061,298 A | * | 10/1991 | Burgoyne et al. | 95/54 |
| 5,076,816 A | * | 12/1991 | Avrillon et al. | 95/51 |
| 5,085,676 A | * | 2/1992 | Ekiner et al. | 96/13 |
| 5,091,216 A | * | 2/1992 | Ekiner et al. | 427/245 |
| 5,112,941 A | * | 5/1992 | Kasai et al. | 528/353 |
| 5,113,867 A | | 5/1992 | Janszen | |
| 5,165,963 A | * | 11/1992 | Matsumoto et al. | 427/245 |
| 5,178,650 A | * | 1/1993 | Hayes | 95/47 |
| 5,234,471 A | * | 8/1993 | Weinberg | 95/47 |
| 5,248,319 A | * | 9/1993 | Ekiner et al. | 95/54 |
| 5,266,100 A | * | 11/1993 | Simmons | 95/43 |
| 5,286,539 A | * | 2/1994 | Kusuki et al. | 96/10 |
| 5,468,430 A | * | 11/1995 | Ekiner et al. | 264/28 |
| 5,591,250 A | * | 1/1997 | Stern et al. | 95/51 |
| 5,605,627 A | | 2/1997 | Carlsen et al. | |
| 5,618,332 A | * | 4/1997 | Ekiner et al. | 95/51 |
| 5,635,067 A | | 6/1997 | Macheras | |
| 5,683,584 A | | 11/1997 | Wenthold et al. | |
| 5,725,769 A | * | 3/1998 | Miller et al. | 210/500.39 |
| 5,749,943 A | * | 5/1998 | Shimazu et al. | 95/50 |
| 5,762,798 A | | 6/1998 | Wenthold et al. | |
| 5,817,165 A | * | 10/1998 | Hachisuka et al. | 96/4 |
| 5,928,410 A | * | 7/1999 | Jois et al. | 95/51 |
| 5,969,087 A | * | 10/1999 | Maeda | 528/353 |
| 6,161,386 A | * | 12/2000 | Lokhandwala | 60/649 |
| 6,180,008 B1 | | 1/2001 | White | |
| 6,187,987 B1 | | 2/2001 | Chin et al. | |
| 6,361,582 B1 | * | 3/2002 | Pinnau et al. | 95/45 |

(Continued)

FOREIGN PATENT DOCUMENTS

EP    0509260 A1 * 10/1992

(Continued)

OTHER PUBLICATIONS

AIChE Journal May 2001 vol. 7, No. 5, Suppression of Gas Separation Membrane Plasticization by Homogenous Polymer Blending.

(Continued)

*Primary Examiner*—Robert H. Spitzer
(74) *Attorney, Agent, or Firm*—Linda K. Russell

(57) ABSTRACT

A method of separating or concentrating hydrocarbon-containing gas mixtures such as hydrogen from hydrocarbons, carbon dioxide from hydrocarbons, nitrogen from hydrocarbons, and hydrocarbons from one another using a selectively permeable membrane. The method is well suited to separate hydrocarbon-containing mixtures such as those generated by petroleum refining industries, petrochemical industries, natural gas processing, and the like. The membranes exhibit extremely good resistance to plasticization by hydrocarbon components in the gas mixture under practical industrial process conditions.

32 Claims, No Drawings

U.S. PATENT DOCUMENTS

| | | | |
|---|---|---|---|
| 6,361,583 B1 * | 3/2002 | Pinnau et al. | 95/45 |
| 6,497,747 B1 * | 12/2002 | Ding et al. | 95/45 |
| 6,602,415 B1 * | 8/2003 | Koros et al. | 210/500.38 |
| 6,630,011 B1 * | 10/2003 | Baker et al. | 95/47 |
| 2002/0104435 A1 * | 8/2002 | Baker et al. | 95/45 |
| 2002/0124722 A1 * | 9/2002 | Baker et al. | 95/45 |
| 2002/0152889 A1 * | 10/2002 | Baker et al. | 95/45 |
| 2002/0170430 A1 * | 11/2002 | Baker et al | 95/45 |
| 2003/0033929 A1 * | 2/2003 | Pinnau et al. | 95/45 |
| 2003/0070545 A1 * | 4/2003 | Liu et al. | 95/45 |
| 2003/0221559 A1 * | 12/2003 | Koros et al. | 96/10 |

FOREIGN PATENT DOCUMENTS

| | | |
|---|---|---|
| EP | EP0732143 | 9/1996 |
| GB | GB1435151 | 12/1979 |

OTHER PUBLICATIONS

Journal of Membrane Science 216 (2003) 195-205, Preparation and Characterization of Highly Selective Dense and Hollow Fiber Asymmetric Membranes Based on BTDA-TDI/MDI co-Polyimide.

Nov. 4, 2004, International Search Report PCT/IB2004/002432.

* cited by examiner

METHOD FOR SEPARATING HYDROCARBON-CONTAINING GAS MIXTURES USING HYDROCARBON-RESISTANT MEMBRANES

RELATED APPLICATIONS

This application is a continuation in part of U.S. patent application Ser. No. 10/642,407 filed 15 Aug. 2003, which is entitled Polyimide Blends for Gas Separation Membranes. That application claims priority to U.S. Provisional Appliccation No. 60/430,275 entitled Polyimide Blends for Gas Separation Membranes that was filed 2 Dec. 2002. This application also claims priority to U.S. Provisional Application No. 60/508,940, that was filed 6 Oct. 2003, and has the same title as this application. This application is also a continuation in part of U.S. patent application Ser. No. 10/353,210, filed 27 Jan. 2003, which claims priority to U.S. Provisional No. 60/430,327, filed on 2 Dec. 2002, that is entitled "Method of Separating Olefins from Mixtures with Paraffins."

FIELD OF THE INVENTION

This invention relates to a method of separating or concentrating hydrocarbon-containing gas mixtures such as hydrogen from hydrocarbons, carbon dioxide from hydrocarbons, nitrogen from hydrocarbons, and hydrocarbons from one another using a selectively permeable membrane. More specifically, it relates to a method of using certain hydrocarbon-resistant polyimide membranes to selectively separate hydrocarbon-containing mixtures such as those generated by petroleum refining industries, petrochemical industries, natural gas processing, and the like.

BACKGROUND OF THE INVENTION

Permselective membranes for gas separation are known and used commercially in applications such as the production of oxygen-enriched air, production of nitrogen-enriched-air for inerting and blanketing, the upgrading of natural gas streams to pipeline quality specifications (e.g., removal of carbon dioxide or nitrogen from raw natural gas), and the recovery of hydrogen from various petrochemical and oil refining streams (e.g., separation of hydrogen from methane, ethane, ethylene, or carbon monoxide). Preferred membranes for industrial gas separations exhibit a combination of high flux and high permselectivity. The separation of gases by polymeric membranes is thought to depend on the size of the gas molecules in relation to the molecular free volume within the polymer structure and the physical or chemical interaction of the gas with the polymer of the membrane. Many polymeric membranes exhibit attractive properties when the permeation performance is measured under ideal conditions; that is, using pure gas samples at relatively low temperature and pressure. Some industrial gas streams to which the membrane may be exposed are at elevated temperatures and/or pressures, and may contain components or impurities that exhibit strong interaction and reaction with the material of the membrane, which may ultimately swell or plasticize the material. Under certain conditions, the membrane may exhibit a reversible or irreversible reduction in flux and/or permselectivity, and ultimately, loss of membrane performance. A membrane with high flux and permselectivity for the gases of interest, and sufficient durability to sustain this performance after long-term contact with aggressive components in these streams under high pressure and temperature is highly desired.

One aspect of the present invention relates to novel gas separation membranes prepared from certain polyimides that possess an excellent balance of gas permeation rates and permselectivity for one gas over other gases in multi-component gas mixtures. Another aspect of the present invention relates to the surprisingly good durability of these when exposed to feed gas containing high levels of higher hydrocarbons. The term "higher hydrocarbon", in the context of this invention, means a hydrocarbon molecule having at least five carbon atoms, and is composed of hydrogen and carbon atoms in straight chain, branched, cyclic or polycyclic configuration, and can be aliphatic or aromatic in nature. For the purpose of nomenclature, the term $C_{5+}$ means a hydrocarbon of at least five carbon atoms, the term $C_{6+}$ means a hydrocarbon of at least six carbon atoms, and the like.

Examples of industrial gas mixtures and processes that are amenable to membrane separation are well known in the art. Membranes have been most successful in applications where the feed stream is primarily bi-component and easy to separate, is relatively free from impurities that could adversely affect the membrane, and is at relatively low temperature and pressure. The economics of the membrane-separation process could be improved substantially if operated at higher temperatures and pressures, and if pretreatment of the feed stream to remove impurities could be eliminated or significantly reduced.

One of the first successful applications for membranes has been the recovery of hydrogen from the vent gas stream in ammonia plants where the feed gas is relatively clean and free of hydrocarbon impurities. Another successful application, again where the feed gas is relatively clean, has been for the removal of hydrogen from synthesis gas streams for adjustment of the hydrogen/carbon monoxide ratio.

Large quantities of hydrogen are consumed in oil refineries; and, much is wasted as fuel gas because it is difficult to recover. Membranes are ideally suited for the recovery of the waste hydrogen; however, most refinery streams contain trace levels of higher hydrocarbons, some of which may be close to their dew point or saturation level at operating conditions.

Membranes are typically two-sided and have a feed side, or a first side, and a permeate side, or a second side. Depending upon a variety of factors, including membrane structure, feed flow rate, and membrane integrity, in some circumstances either side of the membrane can be used for the first side and the second side. When a feed stream containing such components is processed by a membrane system, the hydrogen permeates through the membrane, and the gas on the feed side becomes more concentrated in the higher hydrocarbon components, to a point that may exceed the dew point. These components could condense on the membrane surface, or absorb within the membrane material, and result in swelling or plasticization of the material causing irreversible damage and change in performance. Even at lower contaminant concentration, membrane performance has been reported to decline, presumably due to strong sorption or interaction of the contaminant with the membrane material. In a general sense, aromatic hydrocarbons swell or plasticize polymeric membranes to a greater extent than aliphatic hydrocarbons, and thus must be essentially completely removed from the gaseous feed stream prior to contact with the membrane. Or alternatively, the materials of the membrane must be more resistant to sorption or interaction with contaminants in the streams.

Another application where membranes have had only marginal success is for the removal of carbon dioxide and acid gases from raw natural gas to achieve pipeline quality natural gas (essentially less than about 2.5% carbon dioxide). The major component of raw natural gas is methane, with lesser amounts of carbon dioxide, hydrogen sulfide, other sulfur-containing species, higher hydrocarbons, water, and nitrogen. The nature and purity of the raw gas is dependent on geographic location, geological formation, production history of the well, and the like. The majority of substandard raw gas is purified using chemical sorption systems, but these are costly to build, operate, and maintain. Membrane systems have had limited success in natural gas processing because of the need for extensive pretreatment systems to remove higher aliphatic and aromatic hydrocarbons prior to contact with the membrane. A membrane with improved resistance to hydrocarbons would greatly reduce or eliminate the need for extensive pretreatment, and thus make membranes a viable treatment alternative.

Thus, there remains a need for membranes that will maintain their performance in industrial streams that contain higher hydrocarbons, particularly aromatic hydrocarbons, that are present in refineries and gas fields.

Polyimide membranes are well known in the art. For example, U.S. Pat. No. 4,705,540 discloses highly permeable polyimide gas separation membranes prepared from phenylene diamines having substituents on all positions ortho to the amine functions and a rigid dianhydride or mixtures thereof, specifically pyromellitic dianhydride (PMDA) and 4,4'-(hexafluoroisopropylidene)-bis(phthalic anhydride) (6FDA). These polyimides form membranes with high gas permeabilities but fairly low permselectivities. These polyimides are also sensitive to various organic solvents.

U.S. Pat. No. 4,717,393 shows that polyimides incorporating at least in part 3,3',4,4'-benzophenone tetracarboxylic dianhydride and phenylene diamines having substituents on all positions ortho to the amine functions can be photo chemically crosslinked. Membranes formed from this class of crosslinked polyimides have improved environmental stability and superior gas selectivity than the corresponding crosslinked polyimide. However, photochemical crosslinking is not truly a practical method for fabricating cost-effective gas separation membranes.

U.S. Pat. No. 4,880,442 discloses highly permeable polyimide gas separation membranes prepared from phenylene diamines having substituents on all positions ortho to the amine functions and essentially nonrigid dianhydrides. These polyimides again exhibit high gas permeabilities, but once again low permselectivities.

Bos et. al. (AIChE Journal, 47, 1088 (2001)) report that polymer blends of polyimide Matrimid 5218 (3,3',4,4'-benzophenone tetracarboxylic dianhydride and diaminophenylindane) and copolyimide P84 (copolyimide of 3,3',4,4'-benzophenone tetracarboxylic dianhydride and 80% toluenediisocyanate and 20% 4,4'-methylene-bis(phenylisocyanate) can increase the stability of the membrane against carbon dioxide plasticization when compared to the plain Matrimid 5218 membrane.

Barsema et. al. (Journal of Membrane Science, 216 (2003), p 195–205) report the permeation performance of dense film and asymmetric hollow fiber membranes made from the copolymer derived from reacting benzophenone 3,3',4,4'-tetracarboxylic acid dianhydride (BTDA) with a mixture of toluenediisocyanate and/or 4,4'-methylene-bis (phenylisocyanate).

U.S. Pat. Nos. 4,532,041; 4,571,444; 4,606,903; 4,836,927; 5,133,867; 6,180,008; and 6,187,987 disclose membranes based on a polyimide copolymer derived from the co-condensation of benzophenone 3,3',4,4'-tetracarboxylic acid dianhydride (BTDA) and a mixture of di(4-aminophenyl)methane and a mixture of toluene diamines useful for liquid separations.

U.S. Pat. Nos. 5,605,627; 5,683,584; and 5,762,798 disclose asymmetric, microporous membranes based on a polyimide copolymer derived from the co-condensation of benzophenone-3,3',4,4'-tetracarboxylic acid dianhydride (BTDA) and a mixture of di(4-aminophenyl)methane and a mixture of toluene diamines useful for liquid filtration or dialysis membranes.

U.S. Pat. No. 5,635,067 discloses a fluid separation membrane based on a blend of two distinct polyimides, one being the copolymer derived from the co-condensation of benzophenone 3,3',4,4'-tetracarboxylic acid dianhydride (BTDA) and optionally pyromellitic dianyhdride (PMDA) with a mixture of toluenediisocyanate and/or 4,4'-methylene-bis(phenylisocyanate), and the other being Matrimid 5218.

DETAILED DESCRIPTION OF THE INVENTION

This invention is directed to a method for processing, such as by selectively separating or enriching, a feed mixture of gases containing at least one $C_{5+}$ hydrocarbon component using a membrane containing certain polyimide polymers, copolymers and blends thereof. These polymers have repeating units as shown in the following formula (I), and for the purposes of this invention are classified as Type 1 polyimides:

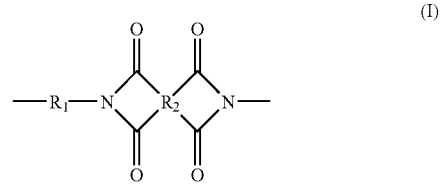

(I)

in which $R_2$ is a moiety selected from the group consisting of formula (A), formula (B), formula (C) and mixtures thereof,

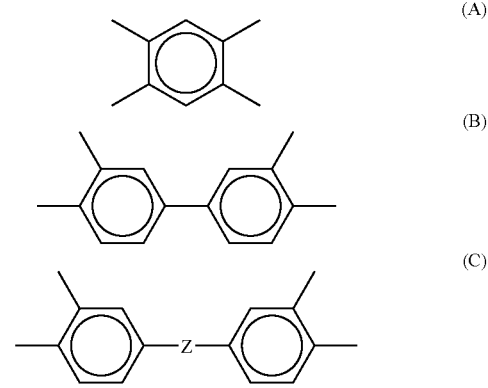

Z is a moiety selected from the group consisting of formula (L), formula (M), formula (N) and mixtures thereof; and

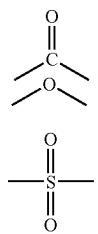

R₁ is a moiety selected from the group consisting of formula (Q), formula (S), formula (T), and mixtures thereof,

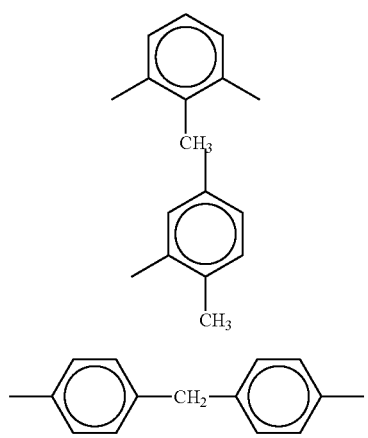

In an embodiment the polyimide that forms the selective layer of the membrane has repeating units as shown in the following formula (Ia):

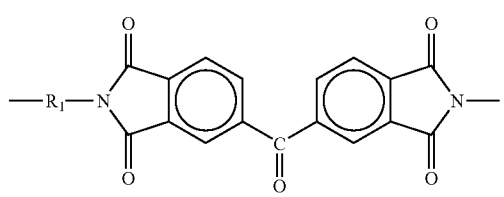

In this embodiment, moiety R₁ is of formula (Q) in 0–100% of the repeating units, of formula (S) in 0–100% of the repeating units, and of formula (T) in a complementary amount totaling 100% of the repeating units. A polymer of this structure is available from HP Polymer GmbH under the trade name P84 and is much preferred for use in the present invention. P84 is believed to have repeating units according to formula (Ia) in which R₁ is formula (Q) in about 16% of the repeating units, formula (S) in about 64% of the repeating units and formula (T) in about 20% of the repeating units. P84 is believed to be derived from the condensation reaction of benzophenone tetracarboxylic dianhydride (BTDA, 100 mole %) with a mixture of 2,4-toluene diisocyanate (2,4-TDI, 64 mole %), 2,6-toluene diisocyanate (2,6-TDI, 16 mole %) and 4,4'-methylene-bis(phenylisocyanate) (MDI, 20 mole %).

As used herein, a "repeating unit" in a polymer is a molecular segment in the polymer chain backbone that repeats itself regularly along the polymer chain. In this respect, the term repeating units is meant to cover all portions of such polymers and any number of the repeating units.

In another embodiment, the polyimide that forms the selective layer comprises repeating units of formula (Ib):

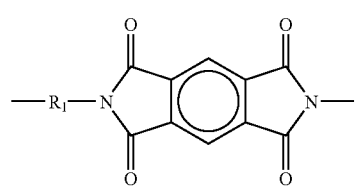

Preference is given to using the Type 1 copolyimide of formula (Ib) in which R₁ is a composition of formula (Q) in about 1–99% of the repeating units, and of formula (S) in a complementary amount totaling 100% of the repeating units.

In yet another embodiment, the copolyimide is a copolymer comprising repeating units of both formula (Ia) and (Ib) in which units of formula (Ib) constitute about 1–99% of the total repeating units of formulas (Ia) and (Ib). A polymer of this structure is available from HP Polymer GmbH under the trade name P84-HT325. It is particularly preferred for use in the present invention. P84-HT325 is believed to have repeating units according to formulas (Ia) and (Ib) in which the moiety R₁ is a composition of formula (Q) in about 20% of the repeating units and of formula (S) in about 80% of the repeating units, and in which repeating units of formula (Ib) constitute about 40% of the total of repeating units of formulas (Ia) and (Ib). P84-HT325 is believed to be derived from the condensation reaction of benzophenone tetracarboxylic dianhydride (BTDA, 60 mole %) and pyromellitic dianhydride (PMDA, 40 mole %) with 2,4-toluene diisocyanate (2,4-TDI, 80 mole %) and 2,6-toluene diisocyanate (2,6-TDI, 20 mole %).

In another embodiment, the polymer that forms the separating layer is comprised of a blend of selected polyimide copolymers. That is, the blends comprise a Type 1 copolyimide as described above, and a Type 2 polyimide as defined more particularly herein. The Type 2 polyimide comprises repeating units having composition of formulas (IIa) and (IIb).

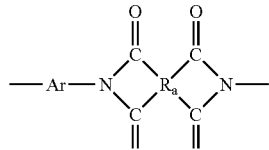

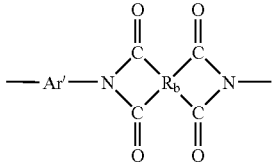

in which Ar is a moiety having composition selected from the group consisting of formula (U), formula (V), and a mixture thereof,

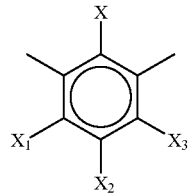
(U)

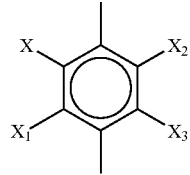
(V)

in which X, $X_1$, $X_2$, $X_3$ independently are hydrogen or alkyl groups having 1 to 6 carbon atoms, provided that at least two of X, $X_1$, $X_2$, $X_3$ on each of (U) and (V) are an alkyl group, Ar' is any aromatic diamine moiety;

$R_a$ and $R_b$ each independently have compositions of formulas (A), (B), (C), (D), or a mixture thereof, and

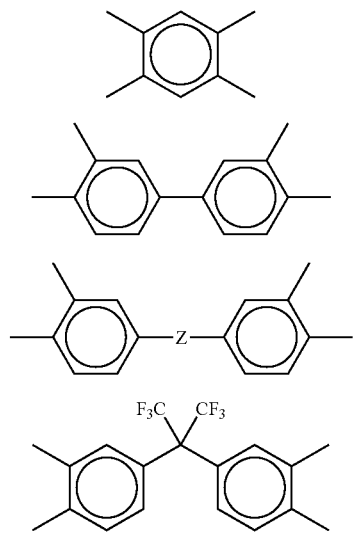
(A)
(B)
(C)
(D)

and Z is a moiety having composition selected from the group consisting of formula (L), formula (M), formula (N), and mixtures thereof.

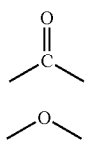
(L)
(M)

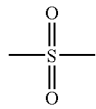
(N)

In the Type 2 polyimide, the repeating unit formula (IIa) should be at least about 25%, preferably at least about 50% of the total repeating units of formula (IIa) and formula (IIb). Ar' can be the same as or different from Ar.

The ratio of Type 1 copolyimide to Type 2 copolyimide in the blend is preferably greater than about 1.0, and more preferably at least about 2.0.

Surprisingly, blends of Type 1 polyimide and Type 2 polyimide are homogeneous over a broad range of compositions. The miscibility of the blends of this invention may be confirmed by the presence of single compositional dependent glass transition temperature lying between those of the constituent blend components. The glass transition temperature can be measured by Differential Scanning Calorimetry or Dynamic Mechanical Analysis.

The polyimides described herein are made by methods well known in the art. Type 1 polyimides can, for example, be conveniently made by polycondensation of an appropriate diisocyanate with approximately an equimolar amount of an appropriate dianhydride. Alternatively, Type 1 polyimides can be, for example, made by polycondensation of equimolar amounts of a dianhydride and a diamine to form a polyamic acid followed by chemical or thermal dehydration to form the polyimide. The diisocyanates, diamines, and dianhydrides useful for making the Type 1 copolyimides of interest are usually available commercially. Type 2 polyimides are typically prepared by the latter diamine process because the diamines are more readily available than the corresponding diisocyanates.

The polyimides should be of suitable molecular weight to be film forming and pliable so as to be capable of being formed into continuous films or membranes. The polyimides of this invention preferably have a weight average molecular weight within the range of about 20,000 to about 400,000 and more preferably about 50,000 to about 300,000.

The preferred Type 1 and Type 2 polyimides are soluble in a wide range of common organic solvents including most amide solvents that are typically used for the formation of polymeric membranes, such as N-methyl pyrrolidone ("NMP"), N,N-dimethyl acetamide ("DMAC"), or highly polar solvents such as m-cresol.

The polymers are usually glassy and rigid, and therefore, may be used to form a single-layer membrane of an unsupported film or fiber. Such single-layer films are normally too thick to yield commercially acceptable flux of the preferentially permeable component of the feed mixture. To be economically practical, the separation membrane usually comprises a very thin selective layer that forms part of a thicker structure. This may be, for example, an integral asymmetric membrane, comprising a dense skin region that forms the selective layer and a micro-porous support region. Such membranes are described, for example, in U.S. Pat. No. 5,015,270 to Ekiner. As a further, and preferred, alternative, the membrane may be a composite membrane, that is, a membrane having multiple layers. Composite membranes typically comprise a porous but non-selective support membrane, which provides mechanical strength, coated with a thin selective layer of another material that is primarily responsible for the separation properties. Typically, such a composite membrane is made by solution-casting (or spinning in the case of hollow fibers) the support membrane, then solution-coating the selective layer in a separate step. Alternatively, hollow-fiber composite membranes can be made by co-extrusion spinning of both the support material and the separating layer simultaneously as described in U.S. Pat. No. 5,085,676 to Ekiner.

The membranes of the invention can be fabricated into any membrane form by any appropriate conventional methods. For illustrative purposes, a method to prepare membranes in accordance with this invention is generally described as follows. Type 1 or a blend of Type 1 and Type 2 copolyimides in dry particulate form is dissolved in a suitable solvent such as N-methylpyrrolidone at approximately about 20–35% polymer content. The polymer solution is cast as a sheet at the desired thickness onto a flat support layer (for flat sheet membranes), or extruded through a conventional hollow fiber spinneret (for hollow fiber membranes). If a uniformly dense membrane is desired, the solvent is slowly removed by heating or other means of evaporation. If an asymmetric membrane is desired, the film or fiber structure is quenched in a liquid that is a non-solvent for the polymer and that is miscible with the solvent for the polyimide. Alternatively, if a composite membrane is desired, the polymer is cast or extruded over a porous support of another material in either flat film or hollow fiber form. The separating layer of the composite membrane can be a dense ultra-thin or asymmetric film.

The resulting membranes may be mounted in any convenient type of housing or vessel adapted to provide a supply of the feed gas, and removal of the permeate and residue gases. The vessel also provides a high-pressure side or first side (for the feed gas and residue gas) and a low-pressure or second side of the membrane (for the permeate gas). For example, flat-sheet membranes can be stacked in plate-and-frame modules or wound in spiral-wound modules. Hollow-fiber membranes are typically potted with a thermoset resin in cylindrical housings. The final membrane separation unit comprises one or more membrane modules, which may be housed individually in pressure vessels or multiple elements may be mounted together in a sealed housing of appropriate diameter and length.

The gases that are produced in industrial plants such as petrochemical plants and refineries that are to be separated may vary widely in composition and character. For example, such feed gases may include but are not limited to the following gases: carbon dioxide, carbon monoxide, sulfide gases such as hydrogen sulfide, paraffins, iso-paraffins, olefins, ozone, argon, chlorine, hydrogen, methane, nitrogen, carbon monoxide, propylene, propane, hexane, and the like commonly found in gases from such sources. Of course, feed gases from any other source and any other composition may be used as long as the membrane is not readily plasticized by any such impurities or other gases or condensates. Further, less selective and more durable membranes or other separation techniques known or used by one skilled in the art may be used to partially separate certain caustic or harmful gases from the feed gases prior to further separation and/or concentration by the membranes disclosed and used herein. In operation, a gas or feed mixture containing at least one $C_{5+}$ hydrocarbon component is contacted with one side of the membrane, such as the first side. Under a suitable driving force for permeation, such as imposing a pressure difference between the feed and permeate sides of the membrane, the more permeable component passes to the permeate side at higher rate than the less permeable component or components. For example hydrogen or carbon dioxide pass to the permeate or second side of the membrane at a higher rate than methane. This produces either a hydrogen-enriched stream or a carbon dioxide-enriched stream on the permeate side of the membrane. The hydrogen- or carbon dioxide-depleted residue, occasionally referred to as the "retentate", is withdrawn from the feed side or first side.

The novel method can operate under a wide range of conditions and is thus adapted to accept a feed stream supplied from diverse sources. If the feed stream is a gas that exists already at a sufficiently high above-atmospheric pressure and a pressure gradient is maintained across the membrane, the driving force for separation can be adequate without raising feed stream pressure farther. Otherwise, the feed stream can be compressed to a higher pressure, a vacuum can be drawn on the permeate or second side of the membrane, or a combination of both can be applied to provide adequate driving force. Preferably the driving force for separation should be a pressure gradient across the membrane of about 0.69 to about 13.8 MPa (100–2000 psi).

This invention is particularly useful for separating hydrogen from methane and/or other hydrocarbons mixtures. Such mixtures are produced as process streams in oil refineries and petrochemical plants, for example. Alternatively, this invention is useful for removing carbon dioxide and other acid gases such as hydrogen sulfide from raw natural gas to produce natural gas of pipeline quality.

An important aspect of this invention is that the membranes maintain a useful level of performance with respect to gas flux and selectivity when exposed to process streams that contain high levels of $C_{5+}$ hydrocarbons. Another aspect of this invention is that any changes in membrane performance in the presence of high levels of $C_{5+}$ hydrocarbons are essentially reversible. In contrast, prior-art membranes often suffer substantial (e.g. >about 30% decline in permeance) irreversible damage during exposure to $C_{5+}$ hydrocarbons. Their performance deteriorates over a relatively short time, requiring replacement of the membranes to reestablish acceptable performance.

To demonstrate the unique resistance of the membranes of this invention to contact with higher hydrocarbons, the materials of the membrane are contacted with liquid hydrocarbons for various times. The sorption of hydrocarbon is determined by % gain in weight. This procedure provides a preliminary measure of the sensitivity of the polymer and membrane to various solvents that might be present in industrial feed streams. To further demonstrate the unique resistance of the membranes of this invention to gas streams containing higher hydrocarbons under simulated industrial process conditions, hollow fiber membranes are tested; at relatively high pressure and temperature, and with various levels of vaporized hydrocarbon injected into the feed stream. Hexane and toluene are selected as hydrocarbons of choice because they are representative of impurities in many industrial process streams of interest, because of the aggressive nature of toluene to most polymeric membranes, and because the test could be run conveniently and reproducibly.

The novel process of this invention comprises various methods of using the membranes of this invention for gas separation and/or enrichment. For example, the invention includes a method for processing a feed mixture of two or more gases wherein the mixture contains at least one $C_{5+}$ hydrocarbon component, wherein the method comprises: (a) providing a selectively permeable membrane wherein the membrane comprises a first side and a second side; (b)

wherein the membrane further comprises at least one polymer or copolymer comprising repeating units of formula (I):

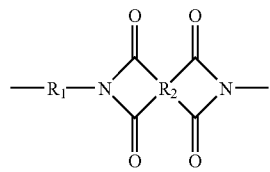
(I)

in which $R_2$ is a moiety having a composition selected from the group consisting of formula (A), formula (B), formula (C), and mixtures thereof,

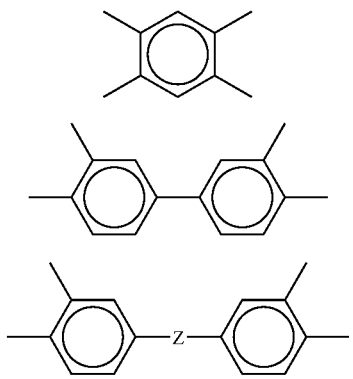
(A)

(B)

(C)

in which Z is a moiety having a composition selected from the group consisting of formula (L), formula (M), formula (N) and mixtures thereof;

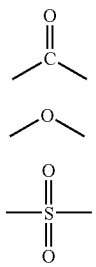
(L)

(M)

(N)

(c) contacting the first side of the membrane with a gaseous feed mixture of at least two or more gas components, wherein the mixture comprises at least one $C_{5+}$ hydrocarbon component; (d) causing at least one component of the feed mixture to selectively permeate through the membrane, thereby forming on the second side of the membrane a permeate composition which has a concentration of at least one component that is greater than the concentration of the feed mixture; (e) removing from the second side of the membrane the permeate composition; and (f) withdrawing from the first side of the membrane a composition which has a concentration of at least one component that is less than the concentration of the feed mixture.

Further in this method, $R_1$ may be a moiety having a composition selected from the group consisting of formula (Q), formula (S), formula (T):

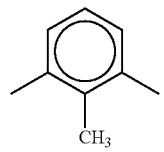
(Q)

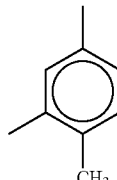
(S)

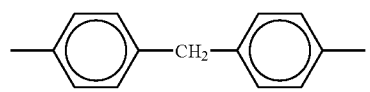
(T)

and mixtures thereof.

In this method, the feed mixture may comprise at least hydrogen and methane. Also in this method, the feed mixture may further comprise at least carbon dioxide and methane. Additionally in this process, the feed mixture may further comprise at least nitrogen and methane.

In addition, the method may further comprise the steps of repeating the foregoing steps (a)–(d) continuously or nearly continuously for at least about 200 hours of operation, wherein after about 200 hours of operation, the membrane exhibits a permeance for the more permeable gas that is at least about 70% of the permeance at an initial time of use.

In this method, the membrane may comprise a composite hollow fiber membrane that comprises a supporting core layer and a gas-separating sheath layer.

Also in this method, the feed mixture may further comprise at least one olefin and at least one paraffin, wherein at least one olefin is separated from the mixture.

Further in this method, the repeating units of formula (I) may comprise repeating units of formula (Ia):

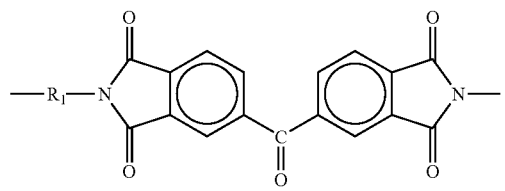
(Ia)

Also in this method, $R_1$ may be comprised of formula (Q) in about 0%–100% of the repeating units, formula (S) is about 0%–100% of the repeating units, and formula (T) in about 0%–100% of the repeating units.

In this method, the repeating units of formula (I) may comprise repeating units of formula (Ib):

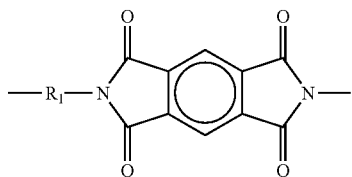

Additionally in this method, the repeating units of formula (I) may comprise repeating units having a composition of formula (Ia) and repeating units having a composition of formula (Ib):

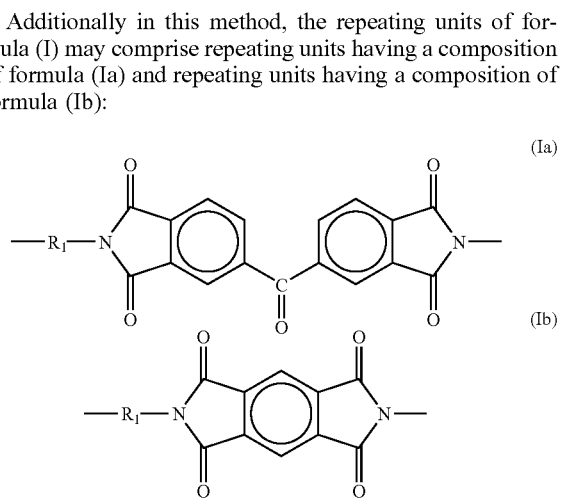

wherein units of formula (Ib) comprise about 1–99% of the total repeating units of formulas (Ia) and (Ib).

Also in this method, $R_1$ may be comprised of formula (Q) in about 1–99% of the repeating units, and $R_1$ may be comprised of formula (S) in a complementary amount so as to total 100%.

Further in this method, the moiety $R_1$ may have a composition of formula (Q) in about 20% of the repeating units, a composition of formula (S) in about 80% of the repeating units, wherein the repeating units of formula (Ib) comprise about 40% of the total of repeating units of formulas (Ia) and (Ib) in formula (I).

Also during this method, at least one $C_{5+}$ hydrocarbon component may condense in liquid form on the first side of the membrane, wherein the first side comprises the feed side of the membrane.

Alternatively and in addition to the foregoing, the method of this invention may comprise a method for processing a feed mixture of two or more gases wherein the mixture contains at least one $C_{5+}$ hydrocarbon component, where the method comprises: (a) providing a gas separation membrane having a first side and a second side, said membrane comprising a blend of at least one polymer of a Type 1 copolyimide and at least one polymer of a Type 2 copolyimide in which the Type 1 copolyimide comprises repeating units of formula (I):

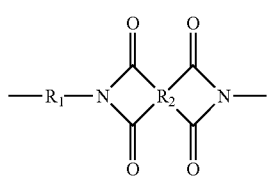

in which $R_1$ is a moiety having a composition selected from the group consisting of formula (Q), formula (S), formula (T), and mixtures thereof,

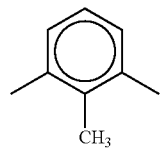

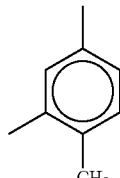

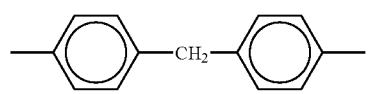

in which the Type 2 copolyimide comprises the repeating units of formulas (IIa) and (IIb)

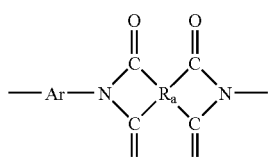

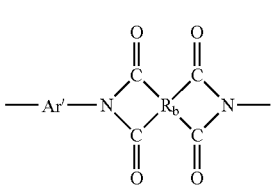

in which Ar is a moiety having a composition selected from the group consisting of formula (U), formula (V):

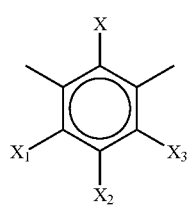

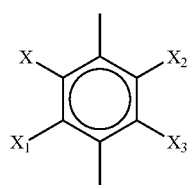

and mixtures thereof. Next in part (b) of the method, the first side of the membrane is contacted with a feed mixture comprising at least one C$_{5+}$ hydrocarbon component. Additional steps of the method are as follows: (c) causing one component of the feed mixture to selectively permeate through the membrane, thereby forming on the second side of the membrane a permeate composition which has a concentration of the one component greater than that of the feed mixture, (d) removing from the second side of the membrane the permeate composition, and (e) withdrawing from the one side of the membrane a composition which has a concentration of the one component that is less than that of the feed mixture.

In this method, R$_2$ may be a moiety having a composition selected from the group consisting of formula (A), formula (B), formula (C) and mixtures thereof, and

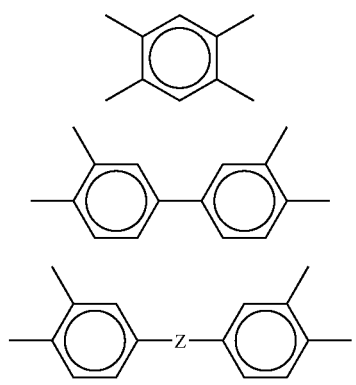

(A)
(B)
(C)

Z is a moiety having a composition selected from the group consisting of formula (L), formula (M), formula (N),

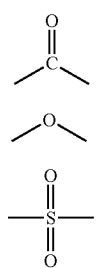

(L)
(M)
(N)

and mixtures thereof.

Further, X, X$_1$, X$_2$, X$_3$ independently are hydrogen or an alkyl group having at least 1 to 6 carbon atoms, provided that at least two of X, X$_1$, X$_2$, or X$_3$ on each of (U) and (V) are an alkyl group, Ar' is any aromatic moiety, R$_a$ and R$_b$ each independently have composition of formulas (A), (B), (C), (D), or mixtures thereof, and

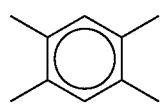

(A)

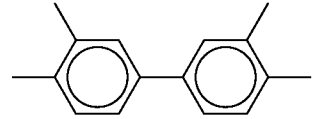

(B)

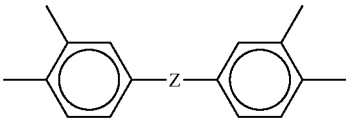

(C)

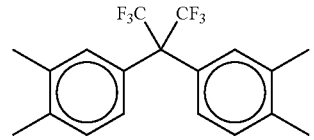

(D)

wherein Z is a moiety having composition selected from the group consisting of formula (L), formula (M), formula (N):

(L)

(M)

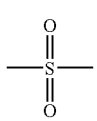

(N)

and mixtures thereof.

Also in this method, the ratio of Type 1 polymer to Type 2 polymer in the blend may be at least about 1.0.

Further, the feed mixture may comprise at least hydrogen and methane, or the feed mixture may comprises at least carbon dioxide and methane, and further, the feed mixture may comprise at least nitrogen and methane. Additionally, the feed mixture may be selected from the group consisting of carbon dioxide; carbon monoxide, sulfide gases such as hydrogen sulfide; paraffins; iso-paraffins; olefins; ozone; nitrogen; argon; chlorine; hydrogen; methane; carbon monoxide; propylene; propane; hexane; and a combination thereof, and the like commonly found in gases from such sources.

Also, the method may further comprise the step of repeating steps (a)–(d) continuously or nearly continuously for at least about 200 hours of operation, wherein after about 200 hours of operation, the membrane exhibits a permeance for the more permeable gas that is at least about 70% of the permeance at an initial time of usage.

Additionally in this method, wherein the membrane may comprise a composite hollow fiber membrane comprised of a supporting core layer and a gas-separating sheath layer.

Also during this method, at least one C$_{5+}$ hydrocarbon component may condense in liquid form on the first side of the membrane and wherein the first side comprises the feed side of the membrane.

Furthermore, the invention may include a method for processing a feed mixture of two or more gases wherein the feed mixture contains at least one C$_{5+}$ hydrocarbon component comprising: (a) providing a composite selectively permeable membrane comprising a core layer with at least a first side and a second side and a gas-separating sheath layer wherein the core layer comprises a polymer or copolymer comprising repeating units of formula (I):

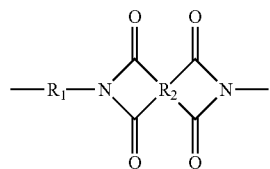
(I)

in which $R_2$ is a moiety having a composition selected from the group consisting of formula (A), formula (B), formula (C) and mixtures thereof,

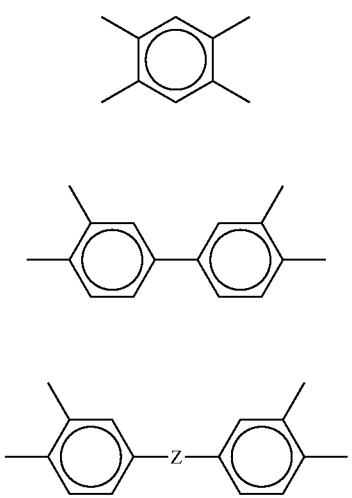
(A)
(B)
(C)

in which Z is a moiety having a composition selected from the group consisting of formula (L), formula (M), formula (N) and mixtures thereof; and

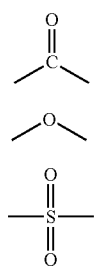
(L)
(M)
(N)

$R_1$ is a moiety having a composition selected from the group consisting of formula (Q), formula (S), formula (T), and mixtures thereof:

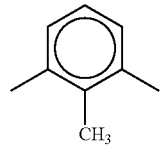
(Q)

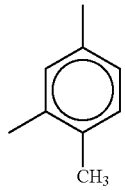
(S)

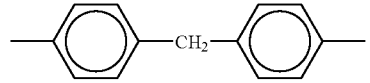
(T)

(b) contacting at least the first side of the membrane with a gaseous feed mixture of at least two or more gas components, wherein the mixture comprises at least one $C_{5+}$ hydrocarbon component, (c) causing at least one component of the feed mixture to selectively permeate through the membrane, thereby forming on the second side of the membrane a permeate composition which has a concentration of at least one component that is greater than the concentration of the feed mixture, (d) removing from the second side of the membrane the permeate composition, and (e) withdrawing from the first side of the membrane a composition which has a concentration of at least one component that is less than the concentration of the feed mixture.

Also as part of this method, the repeating units of formula (I) may comprise repeating units of formula (Ia):

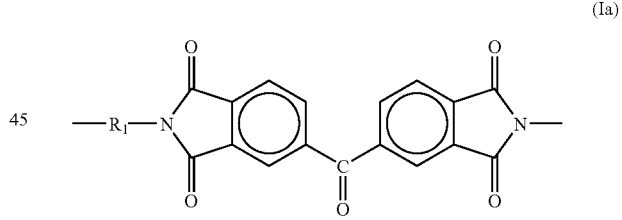
(Ia)

Further in this method, $R_1$ may be comprised of formula (Q) in about 16% of the repeating units, formula (S) in about 64% of the repeating units, and formula (T) in about 20% of the repeating units.

Also in this method, the repeating units of formula (I) may comprise repeating units of formula (Ib):

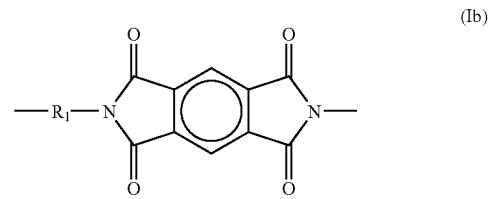
(Ib)

Additionally in this method, the repeating units of formula (I) may comprise repeating units having composition of formula (Ia) and repeating units having composition of formula (Ib):

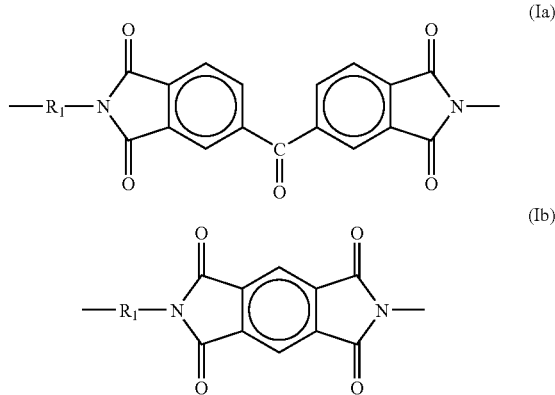

wherein the units of formula (Ib) comprise about 1–99% of the total repeating units of formulas (Ia) and (Ib), and in which $R_1$ is comprised of formula (Q) in about 1–99% of the repeating units, and wherein $R_1$ is comprised of formula (S) in a complementary amount so as to total 100%.

Further in this method, the moiety $R_1$ may have a composition of formula (Q) in about 20% of the repeating units and the composition of formula (S) in about 80% of the repeating units, wherein repeating units of formula (Ib) comprise about 40% of the total of repeating units of formulas (Ia) and (Ib) in formula (I).

Also in this method, the driving force for separation may comprise a pressure gradient across the membrane of about 0.69 MPa to about 13.8 MPa.

As a further aspect of this method, the membrane may comprise at least two permeators. Also, where two permeators are used to separate or concentrate the gas, the average performance of the permeators may be about 3 GPU to about 30 GPU carbon dioxide permeance. Additionally, where two permeators are used to separate or concentrate the gas, the carbon dioxide/nitrogen selectivity ratio may be about 10 to about 25.

Also, the permeation properties of membranes made from polymer blends in general are expressed mathematically in U.S. patent application Ser. No. 10/642,407, which was filed on 15 Aug. 2003, and is entitled "Polyimide Blends for Gas Separation Membranes." The membranes discussed in the foregoing examples are related to membranes disclosed herein for the separation of $C_{5+}$ gases. Additionally, membranes and methods of using such membranes that are especially well suited for the separation of olefins and paraffins are set forth in U.S. patent application Ser. No. 10/353,210, that was filed 27 Jan. 2003, and is entitled "Method of Separating Olefins From Mixtures With Paraffins." The entire disclosures of those U.S. patent applications are incorporated by reference herein.

This invention is now illustrated by examples of certain representative embodiments thereof, wherein parts, proportions and percentages are by weight unless otherwise indicated. All units of weight and measure not originally obtained in SI units have been converted to SI units. The hydrocarbon concentrations in the feed gas are expressed as parts per million (ppm) expressed as the moles of hydrocarbon in a million moles of feed gas. The entire disclosures of U.S. patents set forth in the following examples are hereby incorporated by reference herein.

EXAMPLES

Example 1a

An asymmetric hollow-fiber membrane of P84 was spun from a solution of 30% P84, 9.0%. Tetramethylene sulfone and 1.5% acetic anhydride in N-methylpyrrolidinone (NMP) with methods and equipment as described in U.S. Pat. Nos. 5,034,024 and 5,015,270. The nascent filament was extruded at a rate of 180 cm³/hr through a spinneret with fiber channel dimensions of outer diameter 559 μm, and inner diameter equal to 254 μm at 75° C. A fluid containing 85% NMP in water was injected into the bore of the fiber at a rate of 33 cm³/hr. The nascent fiber traveled through an air gap of 5 cm at room temperature into a water coagulant bath at 24° C. and the fiber was wound up at a rate of 52 m/min.

The water-wet fiber was washed with running water at 50° C. for about 12 hrs to remove residual solvent and then sequentially exchanged with methanol and hexane as taught in U.S. Pat. Nos. 4,080,744 and 4,120,098, followed by vacuum drying at room temperature for 30 minutes and then at 100° C. for one hour. Samples of fiber were formed into four test membrane modules of 52 fibers each. The fiber in the modules was treated to seal defects in the separating layer by a method similar to that described in U.S. Pat. No. 4,230,463. The fiber was contacted with a solution of 2% wt. Sylgard 2577 (Dow Corning Corporation) in 2,2,4-trimethylpentane for 30 minutes and then dried in a vacuum oven for 12–16 hours followed by drying in a convection oven at 70° C. overnight.

The modules were measured in permeation using a feed of carbon dioxide/nitrogen (10:90 mole %) at a temperature of 50° C. and a feed pressure of 5.6 MPa (800 psig). The feed mixture was supplied to contact the outside of the fibers and the permeate stream was collected at atmospheric pressure. The permeate and residue flowrates were measured by volumetric displacement with bubble flowmeters. The feed flowrate was maintained at approximately about 20 times the permeate flowrate. The composition of the permeate, feed, and residue stream was measured using an infrared spectrometer. Permeance and selectivity were calculated using a computer model using feed composition and flow rate, permeate composition and flow rate, feed pressure, and permeate pressure as input data.

The performance of the membrane is expressed in terms of carbon dioxide permeance and carbon dioxide/nitrogen selectivity. The permeance is reported in gas permeation units ("GPU"). One GPU equals $10^{-6}$ cm³ (at standard temperature and pressure "STP")/(sec·cm²·cmHg). The average performance of two permeators was 21.4 GPU carbon dioxide permeance, and carbon dioxide/nitrogen selectivity 14.6.

Example 1b

An asymmetric hollow-fiber membrane of P84 was spun and formed into modules by the same procedure as Example 1a except that it was spun from a solution of 32% P84, 9.6%. Tetramethylene sulfone and 1.6% acetic anhydride in N-methylpyrrolidinone (NMP) into a water coagulant bath at 8° C.

The membrane performance was tested in the same manner as described for Example 1a. The average performance of two P84 based Example 1b permeators was 19.8 GPU carbon dioxide permeance, and carbon dioxide/nitrogen selectivity 16.0.

Example 1c

An asymmetric hollow-fiber membrane of P84 was spun and formed into modules by the same procedure as Example 1b except that it was spun from a solution of 33% P84, 9.9% tetramethylene sulfone and 1.65% acetic anhydride in N-methylpyrrolidinone (NMP) using a spinneret at 96° C. and through an air gap of 5 cm.

The membrane performance was tested in the same manner as described for Example 1a. The average performance of two P84 based Example 1c permeators was 16.0 GPU carbon dioxide permeance, and carbon dioxide/nitrogen selectivity 18.7.

Example 1d

The polyimide PI used was DAM/PMDA:BPDA (1:1). An asymmetric hollow-fiber membrane of P84:PI blend (4:1) was spun and formed into modules by the same procedure as Example 1a except that it was spun from a solution of 31% P84+PI, 9.3% tetramethylene sulfone and 1.55% acetic anhydride in N-methylpyrrolidinone (NMP) using a spinneret at 84° C. and through an air gap of 1 cm. The spinneret had fiber channel dimensions of outer diameter 838 μm and inner diameter equal to 406 μm.

The membrane performance was tested in the same manner as described for Example 1a. The average performance of two P84:PI blend (4:1) based Example 1d permeators was 20.5 GPU carbon dioxide permeance, and carbon dioxide/nitrogen selectivity 16.0.

Example 1e

An asymmetric hollow-fiber membrane of P84 was spun and formed into modules by the same procedure as Example 1a from a solution of 33% P84, and 9.9% tetramethylene sulfone in dimethyl acetamide (DMAc). The spinneret was at 75° C. and its fiber channel dimensions were outer diameter 838 μm and inner diameter equal to 406 μm. The nascent fiber traveled through an air gap of 0.5 cm at room temperature into a water coagulant bath at 25° C. and the fiber was wound up at a rate of 70 m/min.

The membrane performance was tested in the same manner as described for Example 1a. The average performance of a P84 based Example 1e permeator was 27.7 GPU carbon dioxide permeance, and carbon dioxide/nitrogen selectivity 19.5.

Example 1f

An asymmetric hollow-fiber membrane of P84 was spun and formed into modules by the same procedure as Example 1e. The nascent fiber traveled through an air gap of 1.5 cm and the fiber was wound up at a rate of 90 m/min.

The membrane performance was tested in the same manner as described for Example 1a except that the feed pressure was 8.4 MPa (1200 psig). The average performance of a P84 based Example 1f permeator was 10.6 GPU carbon dioxide permeance, and carbon dioxide/nitrogen selectivity 18.0.

Comparative Example 1

Samples of composite hollow-fiber membrane of Matrimid® 5218 a copolymer of 5,x-amino-(4-aminophenyl)-1,1,3 trimethyl indane and 3,3',4,4'-benzophenone tetracarboxylicdianhydride (Vantico, Inc.) were prepared as described in U.S. Pat. No. 5,468,430 (Ekiner, Fleming November 1995). The water-wet fibers were dehydrated and dried as described in Example 1a and fabricated into permeator modules. The modules were further treated to seal defects and then tested as in Example 1a. The average performance of two permeators was 20.0 GPU for carbon dioxide permeance, and a carbon dioxide/nitrogen selectivity 12.0. This initial performance is similar to that of Examples 1a–1f (average of 21.4 GPU/13.7 selectivity).

Comparative Example 2

Samples of hollow-fiber membrane of a polyamide blend (PA1:PA2=6:4) where PA1 comprises a copolymer of diamino mesitylene and isophthalic acid:terephthalic acid (70:30) and PA2 comprises a copolymer of 1,3 phenylene diamine and isophthalic acid:terephthalic acid (70:30) were prepared as described in U.S. Pat. No. 5,091,216.

The water-wet fibers were dehydrated and dried as described in Example 1a, and fabricated into permeator modules. The modules were further post-treated and dried in a vacuum oven at 100° C. for 16 hours and then tested as in Example 1f. The average performance of two permeators was 3.6 GPU for carbon dioxide permeance, and a carbon dioxide/nitrogen selectivity 13.0. This initial permeance is approximately about 33% of that of Example 1f.

Example 2

The permeator modules from Example 1a and Comparative Example 1 were tested for duration of 15 days under the conditions of Example 1a and Comparative Example 1 with the exception that toluene was injected into the feed stream at a concentration of 50 parts per million (ppm)(mole) for the duration of the test. The test was designed to simulate commercial operating conditions in the presence of an aggressive $C_{5+}$ hydrocarbon. The change in $CO_2$ permeance over the duration of the test is shown in Table 1A.

TABLE 1A

| SAMPLE | % Change in $CO_2$ Permeance from Initial |
|---|---|
| Example 1a | −14 |
| Comparative Example 1 | −39 |

The test was continued for another 25 days under the same conditions except that the toluene concentration was increased to 150 ppm (mole). The results are shown in Table 1B.

TABLE 1B

| SAMPLE | % Change in $CO_2$ Permeance from Initial |
|---|---|
| Example 1a | −20 |
| Comparative Example 1 | −48 |

This example clearly shows that the module using the material of this invention (e.g., Example 1a) performed significantly better than the comparative module during toluene exposure.

Example 3

Permeator modules from Example 1b and Comparative Example 1 were tested for duration of 10 days under the conditions of Example 2 with the exception that toluene at a concentration of 50 ppm+hexane at a concentration of 150 ppm were simultaneously injected into the feed stream for the duration of the test. The change in $CO_2$ permeance over the duration of the test is shown in Table 2.

TABLE 2

| SAMPLE | % Change in $CO_2$ Permeance from Initial |
| --- | --- |
| Example 1b | −16 |
| Comparative Example 1 | −35 |

This example clearly shows that the module using the polyimide material of this invention (e.g., Example 1b) performed significantly better than the comparative polyimide module during toluene+hexane exposure.

Comparative Example 3

Samples of hollow-fiber membrane of a polyimide blend (Ultem:Matrimid=9:1) were prepared as described in U.S. Pat. No. 5,468,430. The water-wet fibers were dehydrated and dried as described in Example 1a and fabricated into permeator modules. The modules were further post-treated and dried in a vacuum oven at 100° C.

Example 4

Permeator modules from Examples 1b and 1c and Comparative Examples 1 and 3 were tested for duration of approximately about 5 days under the conditions of Example 1a and Comparative Example 1 with the exception that toluene at a concentration of 150 ppm was injected into the feed stream for the duration of the test. The injection rate was not constant with excursions up to 450 ppm. The toluene injection was then stopped and nitrogen at 1.5 MPa (200 psig) was purged through the permeators for 3 weeks at 50° C. The test was then restarted and the permeator performance was measured with hydrocarbon-free $CO_2/N_2$ feed for a period of 4 days. The change in $CO_2$ permeance after exposure to toluene after the purge is shown in Table 3.

TABLE 3

| SAMPLE | % Change in $CO_2$ Permeance from Initial after purge |
| --- | --- |
| Example 1b | −7 |
| Example 1c | −3 |
| Comparative Example 1 | −61 |
| Comparative Example 3 | −62 |

This example clearly shows that the polyimide membranes of this invention (e.g., Examples 1b and 1c) were more resistant to damage by toluene vapor than the polyimide membranes of Comparative Examples 1 and 3.

Comparative Example 4

Permeator modules from Comparative Example 1 were tested for duration of approximately about 6 days using a feed of carbon dioxide/nitrogen (10:90 mole %) at a temperature of 50° C. and a feed pressure of 5.6 MPa (800 psig) (the same conditions of Example 1a and Comparative Example 1) and toluene at a concentration of 50 ppm was injected into the feed stream for the duration of the test. The toluene injection was then stopped for 98 hrs while the carbon dioxide/nitrogen feed was continued and the performance was measured again at the initial hydrocarbon-free conditions. The change in $CO_2$ permeance over the duration of the test is shown in Table 4.

TABLE 4

| | % Change in $CO_2$ Permeance from Initial | |
| --- | --- | --- |
| SAMPLE | After 10 days exposure to 50 ppm toluene | After Purge |
| Comparative Example 1 | −36 | −29 |

This example shows that the module using the polyimide material of the Comparative Example 1 suffered approximately about 29% non-recoverable permeance loss after exposure to only 50 ppm toluene.

Example 5

Permeator modules from Example Examples 1d, and 1e were tested under the conditions of Example 1a and Comparative Example 1 with the exception that toluene at a concentration of 150 ppm for duration of 19 days and then toluene at a concentration of 450 ppm for duration of 24 days was injected in the feed. The toluene injection was then stopped and the permeator performance was finally measured again at the initial hydrocarbon-free conditions for a further 12 days. The change in $CO_2$ permeance over the duration of the test is shown in Table 5.

TABLE 5

| | % Change in $CO_2$ Permeance from Initial | | |
| --- | --- | --- | --- |
| SAMPLE | After 19 days exposure to 150 ppm toluene | After 24 days exposure to 450 ppm toluene | After Purge |
| Example 1d (23-1, 2) | −18 | −4 | −2 |
| Example 1e | −26 | −51 | −10 |

This example shows that the modules using the material of this invention in blend form (e.g., Example 1d) or neat form (e.g., Example 1e) suffered <10% irreversible loss in permeance when exposed to toluene for 150 ppm and 450 ppm. By contrast, Comparative Example 4 suffered approximately about 29% non-recoverable permeance loss after shorter duration exposure to only 50 ppm toluene.

Example 6

Permeator modules from Example 1f and Comparative Example 2 were tested under the conditions of Example 5 with the exception that the feed pressure was increased to 8.4 MPa (1200 psig). The toluene injection was then stopped and the permeators' performance was finally measured again at the initial hydrocarbon free conditions. The change in $CO_2$ permeance over the duration of the test is shown in Table 6.

TABLE 6

| SAMPLE | % Change in CO$_2$ Permeance from Initial | | |
|---|---|---|---|
| | After 19 days exposure to 150 ppm toluene | After 24 days exposure to 450 ppm toluene | After Purge |
| Example 1f (28-25) | −27 | −54 | −2 |
| Comp. Ex. 2 (156-1, 2) | −17 | −31 | −6 |

This example shows that the modules using the material of this invention (e.g., Example 1f) suffered negligible irreversible loss in permeance when exposed to toluene at 150 ppm and 450 ppm at 8.4 MPa (1200 psig). The permeance was essentially as stable as that of the asymmetric polyaramide fiber of Comparative Example 2. The high permeance of the polyimides of this invention (5× that of typical polyaramides), along with solvent resistance close to that of the polyaramides, give them high commercial value.

Example 7

Jet A fuel (ASTM D 1655), a kerosene-type jet fuel, is a mixture of paraffinic, isoparaffinic, aromatic and napthalenic compounds with carbon numbers ranging from C8–C16 and distillation boiling points ranging from 205° C. to 300° C. Permeator modules from both Example 1e and Comparative Example 1 were first tested using pure nitrogen gas at 0.34 MPa (35 psig) at 82° C. fed through the bore of the fibers. The permeate stream was collected at atmospheric pressure. The feed flowrate was maintained at approximately twice the permeate flowrate. The permeate and residue flowrates were measured by volumetric displacement with bubble flowmeters.

Jet A fuel was then injected into the nitrogen feed stream at a concentration of approximately about 2 parts per million (ppm)(mole) for a period of 9 days. The permeance of the permeator modules of this invention (Example 1e) remained unchanged for the duration of the test; whereas, the permeance of the permeator modules of Comparative Example 1 decreased continually of the 9-day exposure period (Table 6).

Injection of Jet A fuel was then ceased, and the permeators were then again tested with pure nitrogen as the feed under the original conditions.

The permeance of the comparative example permeator modules decreased continually over the 9 days of exposure reaching a nitrogen flux level 45% less than the original unexposed value at 82° C./0.34 MPa (35 psig) of pure nitrogen. After the Jet A fuel injection was stopped, over 10 days, the flux recovered to a flux level 20% less than the original unexposed value. By contrast, the permeance of the similarly exposed modules of this invention (Example 1e) remained constant at the original unexposed pure nitrogen flux level at 82° C./0.34 MPa (35 psig).

TABLE 7

| SAMPLE | % Change in Nitrogen Permeance from Initial | |
|---|---|---|
| | After 9 days exposure to 2 ppm Jet A fuel | After Purge with pure Nitrogen for 10 days |
| Example 1e | No change | No change |
| Comp. Ex. 1 | −45 | −20 |

This example clearly demonstrates that the modules using the material of this invention (e.g., Example 1e) suffered negligible loss in performance when exposed to Jet A fuel; whereas, the permeator modules made from a current state-of-the-art membrane material exhibited a significant and irreversible decline in performance.

Example 8

Films of each polymer were prepared by dissolving the polymer in NMP solvent at about 20 wt % polymer concentration followed by casting onto a glass plate at 100–120° C. using a 38×10$^{-5}$ m (15 mil) knife gap. The film was dried on the plate at this temperature for 1–2 hours, removed from the plate, cooled to room temperature and air-dried overnight. The film was further dried in a vacuum oven at about 68 kPa (20 inches Hg) at 220° C. for 3 days under a nitrogen atmosphere. A final film thickness of between 2×10$^{-5}$ and 5×10$^{-5}$ m (1–2 mils) was thus obtained. Samples (5 cm×5 cm) of each film were immersed in n-hexane or toluene for 30 days at room temperature. The samples were removed from the solvent, patted dry with a paper towel, and then weighed. Percent solvent uptake is reported as the % gain in weight versus the film prior to immersion in Table 8.

TABLE 8

| Sample | % Weight gain for each solvent | |
|---|---|---|
| | n-hexane | toluene |
| TDI + BTDA/BPDA(60/40) | 0 | 0.7 |
| TDI + BTDA/PMDA(60/40) | 0.3 | 1.5 |
| P84 + [DAM + PMDA/BPDA(50/50)] 1:1 | 0 | 25.5 |
| P84 + [DAM + PMDA/DSDA(50/50)] 1:1 | 0 | 13.8 |
| P84 + [DAM + PMDA/BTDA(86/14)] 3:1 | 0 | 0 |
| P84 + [DAM + PMDA/DSDA(86/14)] 3:1 | 0 | 0.6 |
| P84 + [DAM + PMDA/BPDA(75/25)] 3:1 | 0 | 1.6 |
| Matrimid 5218 Polyimide | 1.0 | 41 |
| Cellulose acetate | 0.3 | 17 |
| Polysulfone | NM | Attacked - strongly swells and softens |

It is clear from Table 8 that the Type 1 polyimides exhibit very low solvent uptake compared to the polymers currently used for state-of-the-art gas separation membranes. Blends of Type 1 polyimides with Type 2 polyimides also exhibit excellent solvent uptake as long as the blend is comprised of at least 50% Type 1 polymer.

Although specific forms of the invention have been selected for illustration in the preceding description is drawn in specific terms for the purpose of describing these forms of the invention fully and amply for one of average skill in the pertinent art, it should be understood that various substitutions and modifications which bring about substantially equivalent or superior results and/or performance are deemed to be within the scope and spirit of the following claims.

What is claimed is:

1. A method for processing a feed, said method comprising:
(a) providing a selectively permeable membrane wherein said membrane comprises a first side and a second side, wherein said membrane further comprises at least one polymer or copolymer comprising a repeating unit of formula (I):

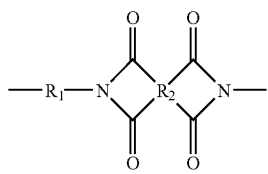
(I)

in which R₂ is a moiety having a composition formula (C),

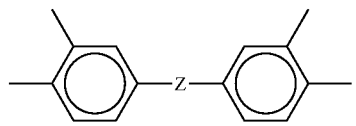
(C)

in which Z is a moiety having a composition formula (M),

(M)

and in which R₁ is a moiety having a composition selected from the group consisting of formula (Q), formula (S), formula (T), and mixtures thereof,

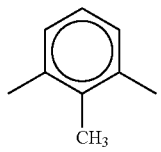
(Q)

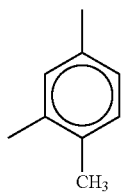
(S)

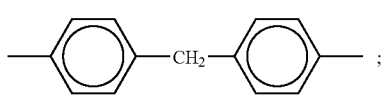
(T)

b) contacting said first side of said membrane with a gaseous feed mixture of at least two or more gas components;

c) causing at least one component of said gaseous feed mixture to selectively permeate through the membrane, thereby forming on said second side of said membrane a permeate composition which has a concentration of at least one component that is greater than the concentration of said gaseous feed mixture;

d) removing from said second side of said membrane said permeate composition; and e) withdrawing from said first side of said membrane a composition, which has a concentration of at least one component that is less than the concentration of said gaseous feed mixture.

2. The method of claim 1, wherein said gaseous feed mixture further comprises at least hydrogen and methane.

3. The method of claim 1, wherein said gaseous feed mixture further comprises at least carbon dioxide and methane.

4. The method of claim 1, wherein said gaseous feed mixture further comprises at least nitrogen and methane.

5. The method of claim 1, further comprising the steps of repeating steps (a)–(e) continuously or nearly continuously for at least about 200 hours of operation, wherein after about 200 hours of operation, said membrane exhibits a permeance for said at least one component that is at least about 70% of the permeance of said at least one component at an initial time of use.

6. The method of claim 1, wherein said membrane comprises a composite hollow fiber membrane comprising a supporting core layer and a gas-separating sheath layer.

7. The method of claim 1, wherein said gaseous feed mixture further comprises at least one olefin and at least one paraffin, and wherein at least one olefin is separated from said mixture.

8. The method of claim 1, wherein said gaseous feed mixture comprises at least one $C_{5+}$ hydrocarbon component, and wherein said at least one $C_{5+}$ hydrocarbon component condenses in liquid form on said first side of said membrane and wherein said first side comprises the feed side of said membrane.

9. A method for processing a feed, said method comprising:
(a) providing a selectively permeable membrane wherein said membrane comprises a first side and a second side, wherein said membrane further comprises at least one polymer or copolymer comprising a repeating unit of formula (I):

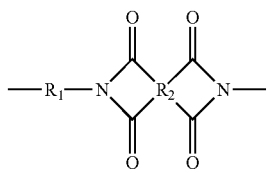
(I)

in which R₂ is a moiety having a composition selected from the group consisting of formula (A), formula (B), formula (C), and mixtures thereof,

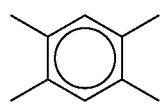
(A)

-continued

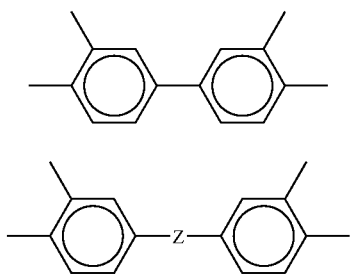

(B)

(C)

in which Z is a moiety having a composition selected from the group consisting of formula (L), formula (M), formula (N) and mixtures thereof,

(L)

(M)

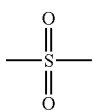

(N)

wherein $R_1$ is a moiety formula (S):

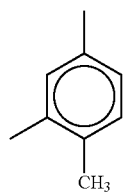

(S)

(b) contacting said first side of said membrane with a gaseous feed mixture of at least two or more gas components;
(c) causing at least one component of said gaseous feed mixture to selectively permeate through said membrane, thereby forming on said second side of said membrane a permeate composition with a concentration of said at least one component that is greater than a concentration of said at least one component in said gaseous feed mixture;
(d) removing from said second side of said membrane said permeate composition; and
(e) withdrawing from said first side of said membrane a composition which has a concentration of said at least one component that is less than a concentration of said at least one component in said gaseous feed mixture.

10. The method of claim 9, wherein said repeating unit of formula (I) comprises repeating units of formula (Ia):

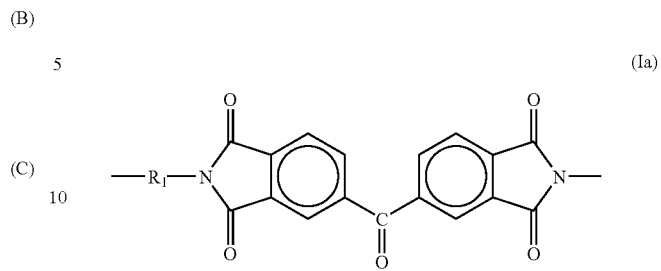

(Ia)

wherein $R_1$ is a moiety as defined above.

11. A method for processing a feed, said method comprising:
(a) providing a selectively permeable membrane wherein said membrane comprises a first side and a second side, and wherein said membrane further comprises at least one polymer or copolymer comprising a plurality of repeating units having a composition of formula (Ia) and a composition of formula (Ib):

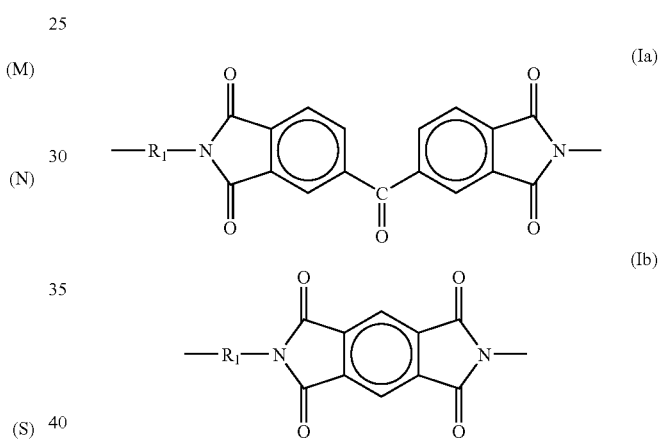

(Ia)

(Ib)

wherein $R_1$ is a moiety having a composition selected from the group consisting of formula (Q), formula (S), formula (T):

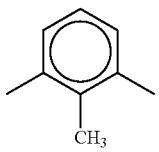

(Q)

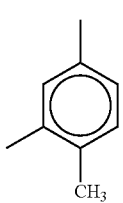

(S)

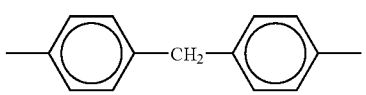

(T)

and mixtures thereof, wherein units of formula (Ib) comprise about 1–99% of the total of said repeating units of formulas (Ia) and (Ib);

(b) contacting said first side of said membrane with a gaseous feed mixture of at least two or more gas components;

(c) causing at least one component of said feed mixture to selectively permeate through said membrane, thereby forming on said second side of said membrane a permeate composition which has a concentration of said at least one component that is greater than a concentration of said at least one component in said feed mixture;

(d) removing from said second side of said membrane said permeate composition; and (e) withdrawing from said first side of said membrane a composition which has a concentration of said at least one component that is less than a concentration of said at least one component in said gaseous feed mixture.

12. The method of claim 11, wherein $R_1$ is comprised of formula (Q) in about 1–99% of said repeating units, and wherein $R_1$ is comprised of formula (S) in a complementary amount so as to total 100%.

13. The method of claim 11, in which $R_1$ has a composition of formula (Q) in about 20% of said repeating units, wherein $R_1$ has a composition of formula (S) in about 80% of said repeating units, and wherein said repeating units of formula (Ib) comprise about 40% of the total of said repeating units of formulas (Ia) and (Ib).

14. A method for processing a feed, said method comprising:

(a) providing a gas separation membrane having a first side and a second side, said membrane comprising a blend of at least one polymer of a Type 1 copolyimide and at least one polymer of a Type 2 copolyimide in which the Type 1 copolyimide comprises a repeating unit of formula (I):

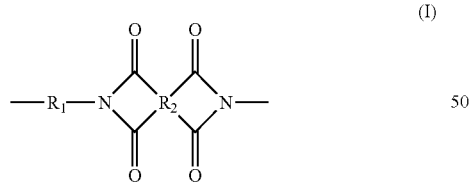

(I)

in which $R_1$ is a moiety having a composition selected from the group consisting of formula (Q), formula (S), formula (T), and mixtures thereof,

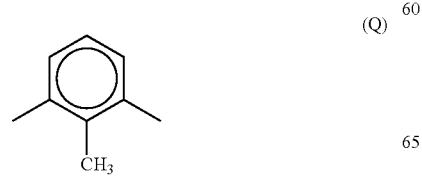

(Q)

-continued

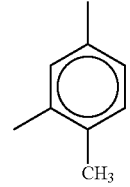

(S)

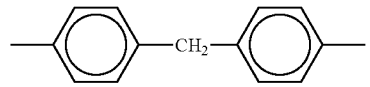

(T)

and $R_2$ is a moiety having a composition selected from the group of consisting of formula (A), formula (B), formula (C), and mixtures thereof,

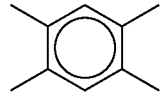

(A)

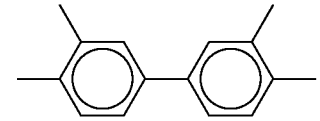

(B)

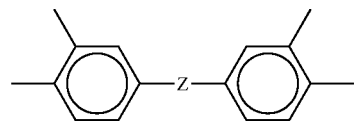

(C)

in which Z is a moiety having a composition selected from the group consisting of formula (L), formula (M), formula (N) and mixtures thereof;

(L)

(M)

(N)

in which the Type 2 copolyimide comprises a Type 2 repeating unit of formulas (IIa) and (IIb)

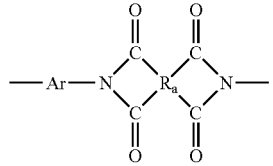

(IIa)

-continued

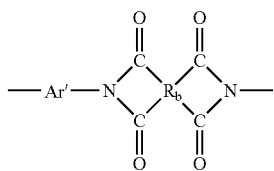

(IIb)

in which Ar is a moiety having a composition selected from the group consisting of formula (U), formula (V):

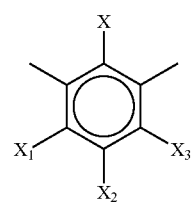

(U)

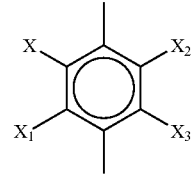

(V)

and mixtures thereof, in which X, $X_1$, $X_2$, $X_3$ are selected independently from the group consisting of hydrogen and alkyl groups having 1 to 6 carbon atoms, and in which at least two of X, $X_1$, $X_{2, X3}$ in each of the formula (U) and the formula (V) are an alkyl group, in which Ar' is an aromatic diamine moiety, and in which $R_a$ and $R_b$ are each selected independently from the group consisting of formula (A), formula (B), formula (C), formula (D),

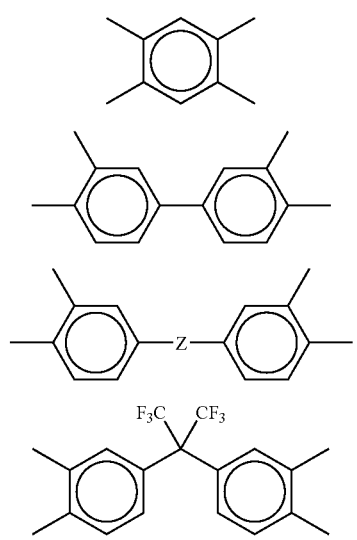

and mixtures thereof, wherein Z is as defined above;

(b) contacting said first side of said membrane with a feed mixture comprising at least one $C_{5+}$ hydrocarbon component;

(c) causing at least one component of said feed mixture to selectively permeate through said membrane, thereby forming on said second side of said membrane a permeate composition which has a concentration of said at least one component greater than a concentration of said at least one component in said feed mixture;

(d) removing from said second side of said membrane said permeate composition; and (e) withdrawing from said first side of said membrane a composition which has a concentration of said at least one component that is less than a concentration of said at least one component in said feed mixture.

15. The method of claim 14, wherein a ratio of Type 1 polymer to Type 2 polymer in the blend is at least about 1.0.

16. The method of claim 14, wherein said feed mixture comprises at least hydrogen and methane.

17. The method of claim 14, wherein said feed mixture comprises at least carbon dioxide and methane.

18. The method of claim 14, wherein said feed mixture comprises at least nitrogen and methane.

19. The method of claim 14, wherein said feed mixture is selected from the group consisting of carbon dioxide; carbon monoxide; sulfide gases; hydrogen sulfide; paraffins; isoparaffins; olefins; ozone; argon; chlorine; hydrogen; methane; nitrogen; carbon monoxide; propylene; propane; hexane; and mixtures thereof.

20. The method of claim 14, further comprising the step of repeating steps (a)–(e) continuously or nearly continuously for at least about 200 hours of operation, wherein after about 200 hours of operation, the membrane exhibits a permeance for said at least one component that is at least about 70% of the permeance of said at least one component at an initial time of usage.

21. The method of claim 14, wherein said membrane comprises a composite hollow fiber membrane comprised of a supporting core layer and a gas-separating sheath layer.

22. The method of claim 14, wherein at least one of said at least one $C_{5+}$ hydrocarbon components condenses in liquid form on said first side of the membrane and wherein said feed mixture is fed to said first side of said membrane.

23. A method for processing a feed, said method comprising:

(a) providing a composite selectively permeable membrane comprising a corelayer with at least a first side and a second side and a gas-separating sheath layer wherein said core layer comprises a polymer or copolymer comprising a repeating unit of formula (I):

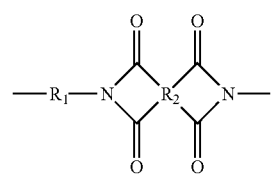

(I)

in which $R_2$ is a moiety having a composition selected from the group consisting of formula (A), formula (B), formula (C) and mixtures thereof,

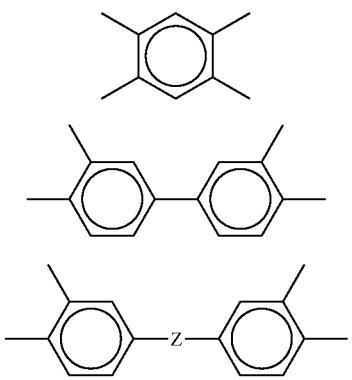

(A)

(B)

(C)

in which Z is a moiety having a composition selected from the group consisting of formula (L), formula (M), formula (N) and mixtures thereof; and

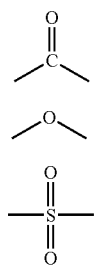

(L)

(M)

(N)

$R_1$ is a moiety having a composition selected from the group consisting of formula (Q), formula (S), formula (T), and mixtures thereof:

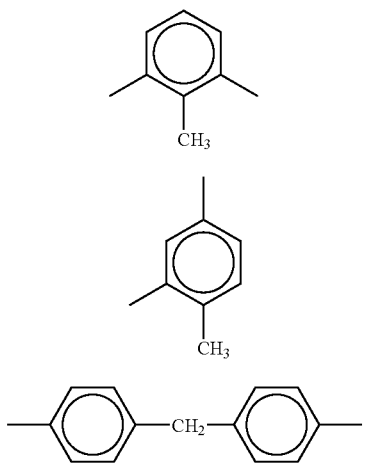

(Q)

(S)

(T)

(b) contacting at least said first side of said membrane with a gaseous feed mixture of at least two or more gas components, wherein said gaseous feed mixture comprises at least one $C_{5+}$ hydrocarbon component;

(c) causing at least one component of said gaseous feed mixture to selectively permeate through said membrane, thereby forming on said second side of the membrane a permeate composition which has a concentration of said at least one component that is greater than the concentration of said gaseous feed mixture;

(d) removing from said second side of said membrane said permeate composition; and (e) withdrawing from said first side of said membrane a composition which has a concentration of said at least one component that is less than the concentration of said at least one component in said gaseous feed mixture.

24. The method of claim 23, in which said repeating unit of formula (I) comprises repeating units of formula (Ia):

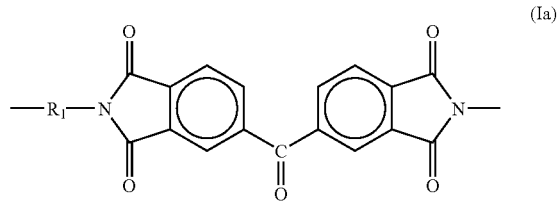

(Ia)

25. The method of claim 24, in which $R_1$ is comprised of formula (Q) in about 16% of said repeating units, formula (S) in about 64% of said repeating units, and formula (T) in about 20% of said repeating units.

26. The method of claim 23, in which said repeating unit of formula (I) comprises repeating units of formula (Ib):

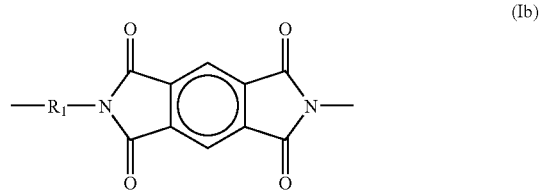

(Ib)

27. The method of claim 23, in which said repeating units of formula (I) comprise a plurality of repeating units having a composition of formula (Ia) and a composition of formula (Ib):

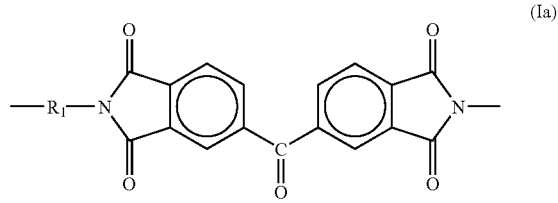

(Ia)

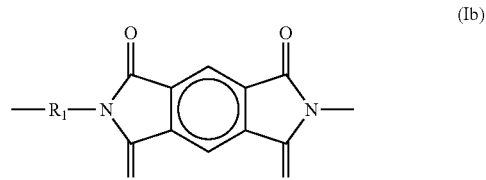

(Ib)

wherein units of formula (Ib) comprise about 1–99% of the total of said repeating units of formulas (Ia) and (Ib), and in which $R_1$ is comprised of formula (Q) in about 1–99% of said repeating units, and wherein $R_1$ is comprised of formula (S) in a complementary amount so as to total 100%.

28. The method of claim 27, in which $R_1$ has a composition of formula (Q) in about 20% of said repeating units, and wherein $R_1$ has a composition of formula (S) in about 80% of said repeating units, and wherein repeating units of formula (Ib) comprise about 40% of the total of said repeating units of formulas (Ia) and (Ib) in formula (I).

29. The method of claim 23, wherein the driving force for separation comprises a pressure gradient across said membrane of about 0.69 MPa to about 13.8 MPa.

30. The method of claim 23, wherein said membrane provided is contained in a plurality of permeators.

31. The method of claim 30, wherein said permeators are used to separate or concentrate said gaseous feed mixture and wherein an average performance of said permeators is about 3 GPU to about 30 GPU carbon dioxide permeance.

32. The method of claim 30, wherein said permeators are used to separate or concentrate said gaseous feed mixture and wherein a carbon dioxide/nitrogen selectivity ratio is about 10 to about 25.

* * * * *